United States Patent
Richard

(10) Patent No.: US 6,300,473 B1
(45) Date of Patent: Oct. 9, 2001

(54) SLM-1: A NOVEL SAM68-LIKE MAMMALIAN PROTEIN

(75) Inventor: Stéphane Richard, Montreal (CA)

(73) Assignee: The Sir Mortimer B. Davis - Jewish General Hospital, Montreal (CA)

(*) Notice: Subject to any disclaimer, the term of this patent is extended or adjusted under 35 U.S.C. 154(b) by 0 days.

(21) Appl. No.: 09/343,011

(22) Filed: Jun. 29, 1999

(30) Foreign Application Priority Data

Mar. 12, 1999 (CA) .................................................. 2265217

(51) Int. Cl.⁷ ...................................................... C07K 1/00
(52) U.S. Cl. ........................... 530/350; 530/324; 530/352
(58) Field of Search .................................. 530/300, 326, 530/350, 324, 325, 352; 435/4, 7.1, 7.4, 7.8

(56) References Cited

U.S. PATENT DOCUMENTS 5,610,276  3/1997  Wong et al. ........................... 530/350

OTHER PUBLICATIONS

Lee, J.–S., et al. Genbank Accession No. 075525. "Salp alpha, SAM68–like phosphotyrosine protein alpha.", Nov. 1998.*

Vernet, C. et al. Genbank Accession No. 088624. "Etoile encodes an RNA–binding protein related to the Sam68 protein and implicated in the STAR pathway", Nov. 1998.*

Bowie, J.U. et al. Deciphering the Message in Protein Sequences: Tolerance to Amino Acid Substitutions. Science 247:1306–1310, Mar. 1990.*

Ngo, J.T. et al. Computational Complexity, Protein Structure Prediction, and The Levinthal Paradox in the Protein Folding Problem and Tertiary Structure Prediction (Merz, ed.), pp. 433, and 492–495, 1994.*

Frommel, C. et al. An Estimate on the Effect of Point Mutation and Natural Selection on the Rate of Amino Acid Replacement in Proteins. Journal of Molecular Evolution 21:233–257, Nov. 1998.*

Database GenBank Accession No. AF069681 Jul. 1, 1998 Venables, J.P. et al Homo sapiens T–Star mRNA.

Database GenBank Accession No. AF079763 Aug. 14, 1998 Venables, J.P. et al. Mus Musculus ETOILE mRNA.

Database GenBank Accession No. AF099092 Nov. 3, 1998 Mus Musculus SLM–2 mRNA Di Fruscio, M. et al.

* cited by examiner

Primary Examiner—Scott D. Priebe
Assistant Examiner—Richard Schnizer
(74) Attorney, Agent, or Firm—BakerBotts LLP

(57) ABSTRACT

The present invention relates to two Sam68-like mammalian proteins, namely SLM-1 and SLM-2, and nucleic acid molecules encoding them. The invention also relates to expression vectors and cells capable of expressing the proteins and antibodies capable of specifically binding to the proteins. Kits for the assay of tyrosine kinase activity are discussed which may be used to determine whether or not a cell is cancerous. The present invention further relates to transgenic animals such as "knockout mice". Knockout mice may be used to study the effect of test compounds on SLM-1 or SLM-2 deficiency.

4 Claims, No Drawings

SLM-1: A NOVEL SAM68-LIKE MAMMALIAN PROTEIN

FIELD OF THE INVENTION

This invention relates to the field of signal transduction proteins, in particular, proteins related to Sam68.

BACKGROUND OF THE INVENTION

The binding of ligands to cell surface receptors can stimulate specific enzymatic activities in the cell. In certain cases, the 'signal' is transduced directly by the receptor which becomes capable of carrying out certain enzymatic functions. In other cases, the receptor triggers other proteins to carry out such enzymatic functions. The proteins which are modified by such activity are known as signal transduction proteins. Enzymatic activity stimulated includes tyrosine kinase (Pawson, Nature 373:573, 1995) and arginine methylase activity (Gary and Clarke, 1998, Prog Nucleic Acid Res. Mol. Biol. 61:65). It is known that many growth factor receptors and soluble tyrosine kinases are oncogenes and can transform cells. Thus, substrates of tyrosine kinases or the presence of post-translation modifications, such as arginine methylation, in response to growth factor receptors can serve as an indication of whether or not a cell is cancerous.

Signal transduction molecules often contain proline motifs and phosphotyrosine residues that serve as specific binding sites for Src-homology-3 (SH3) and Src-homology-2 (SH2) domain containing proteins (Pawson, Nature 373:573, 1995). SH2 recognizes peptides bearing phosphotyrosine (pTyr), and SH3 recognizes sequences containing one or more proline residues.

Sam68 (Src substrate activated during mitosis of 68 kDa), previously called p62 (GAP associated protein of 62 kDa) (Wong et al. (1992) Cell 69:551) is a signal transduction protein. It associates with SH2 and SH3 binding domains, for example those contained in certain tyrosine kinases. It can also bind single-stranded RNA (ssRNA), single-stranded DNA (ssDNA) and double-stranded DNA (dsDNA).

SUMMARY OF THE INVENTION

In one aspect, the invention provides a purified and isolated polypeptide comprising an amino acid sequence of at least 20 consecutive amino acids from the amino acid sequence of SEQ ID NO:1 or SEQ ID NO:2.

In another aspect, the invention provides a polynucleotide encoding a polypeptide of the invention.

In another aspect, the invention provides an expression vector comprising a polynucleotide of the invention.

In a further aspect, the invention provides a cell which has been transformed to express a polynucleotide of the invention.

In another aspect, the invention provides an antibody capable of specifically binding to a polypeptide of the invention.

In another aspect, the invention provides an animal cell which has been genetically modified such that its endogeneous gene coding for SLM-1 is incapable of expression. In another aspect, the invention provides an animal cell which has been genetically modified such that its endogeneous gene coding for SLM-2 is incapable of expression.

In a further aspect, the invention provides an animal which has been gentically modified such that its endogenous gene coding for SLM-1 is incapable of expression in certain tissue specific cells. In a further aspect, the invention provides an animal which has been gentically modified such that its endogenous gene coding for SLM-2 is incapable of expression in certain tissue specific cells.

In another aspect, the invention provides a commercial package for the assay of tyrosine kinase activity comprising a polypeptide of the invention together with instructions for its use.

In another aspect, the invention provides a commercial package for the assay of tyrosine kinase activity comprising an antibody of the invention, together with instructions for its use.

DESCRIPTION OF PREFERRED EMBODIMENTS OF THE INVENTION

SLM-1 and SLM-2 are Sam68-like mammalian proteins.

SLM-1 is a substrate for both tyrosine kinases and protein arginine methyltransferases and it has the property of binding many SH3 and SH2 domain containing proteins including Src kinases, Grb2, p120rasGAP and PLCg1. SLM-1 is a protein that is expressed ubiquitously in mammalian cells and functions as an RNA binding protein, binding poly U and poly A homopolymeric RNA.

SLM-2 is an RNA binding protein that shares the same signaling motifs as SLM-1 and Sam68. It is a substrate for both certain tyrosine kinases and protein arginine methyltransferases and it has the property of binding many SH3 and SH3 domain containing proteins. It binds poly G and poly A homopolymeric RNA. It is expressed mainly in the brain and skeletal muscle.

Peptide Sequences. The present invention provides for purified SLM-1 as well as SLM-1 derivatives that possess the biological and/or immunological properties of SLM-1. The present invention also provides for purified SLM-2 as well as SLM-2 derivatives that possess the biological and/or immunological properties of SLM-2.

The subject invention also encompasses polynucleotides that have the biological activity of SLM-1 or SLM-2 and an amino acid sequence identical or homologous to SLM-1 or SLM2, respectively. The nucleotide sequences encoding homologous proteins are capable of hybridizing to the nucleotide sequence encoding SLM-1 or SLM-2 under low stringency conditions, such as 40%-50% formamide, 37–42° C., 4X SSC, and wash conditions (after several room temperature washes with 2X SSC, 0.5% SDS) of stringency equivalent to 37° C. with 1×SSC, 0.05% SDS.

The biological activities of SLM-1 and SLM-2 include: (1) the property of serving as a substrate for one or more enzymes with tyrosine kinase activity, such as p60Src and p59fyn, (2) the property of serving as a substrate for enzymes with arginine methyltransferase activity, including such enzymes as protein arginine N-methyl transferases including PRMT1, PRMT2, and PRMT3, (3) the property of binding Src kinases, Src derivatives, or molecules with tyrosine kinase activity, e.g., when at least partially tyrosine phosphorylated, (4) the property of binding SH3 and SH2 domain containing proteins including Grb2, PLCg1, p120rasGAP and Grb2, e.g., when at least partially tyrosine phosphorylated, and (5) the property of associating with RNA.

SLM-1 and SLM-2 may be phosphorylated or non-phosphorylated as well as methylated or non-methylated. Phosphorylated SLM-1 or SLM-2 possess one or more phosphorylated tyrosine residues; methylated SLM-1 or SLM-2 possess one or more methylated arginine residues.

The amino acid sequences of mouse SLM-1 and SLM-2 were determined and are given herein as SEQ ID NO:1 and SEQ ID NO:2, respectively. It will be appreciated that SLM-1 and SLM-2 from species other than mouse, including humans, may have amino acid sequences that differ from the mouse sequences, but still possess SLM-1 or SLM-2 biological activity.

SLM-1 or SLM-2 derivatives include polypeptides possessing SLM-1 or SLM-2 biological activity and/or SLM-1 or SLM-2 immunological activity, respectively. A polypeptide possessing SLM-1 immunological activity can specifically bind with antibodies specific for SLM-1, or can, upon injection with suitable adjuvants, be used to induce an immune response specific for SLM-1. A polypeptide possessing SLM-2 immunological activity can specifically bind with antibodies specific for SLM-2, or can, upon injection with suitable adjuvants, be used to induce an immune response specific for SLM-2.

Derivatives of SLM-1 or SLM-2 include polypeptides which have the amino acid sequence of SLM-1 or SLM-2, but with one or more amino acid substitutions. It will of course be understood, without the intention of being limited thereby, that a variety of substitutions of amino acids is possible while preserving the structure responsible for the biological activity of the proteins disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology, i.e., sequence identity, of a variant protein with a naturally occurring protein, the greater the retention of metabolic activity.

Derivatives also include polypeptides with various minor amino acid deletions and/or insertions, typically in the range of about 1 to 5 amino acids.

Other SLM-1 or SLM-2 derivatives may contain stretches of amino acid sequences that lack significant homology to SLM-1 or SLM-2 but still possess one or more biological activities of interest, or immunological activity.

SLM-1, SLM-2 and their derivatives may be derivatized by covalently attaching modifying molecules that are not part of the polypeptide backbone of SLM-1 or SLM-1 derivatives. The modifying molecules may be attached by either or both of biological (i.e., enzymatic) and synthetic means. Modifying molecules may include carbohydrates, lipids, water soluble polymers, or the like. SLM-1 and SLM-2 derivatives may possess glycosylation patterns that vary in accordance with the type of cell in which they are produced.

Nucleotide Sequences. In one aspect, the invention provides for purified nucleotide sequences encoding all or a portion of SLM-1, SLM-2, or their derivatives. Such nucleotide sequences include those composed of DNA and their complementary RNA sequences.

The nucleotide sequences SEQ ID NO:3 and SEQ ID NO:4 represent the mouse nucleotide sequences encoding the polypeptide sequences of SEQ ID NO:1 and SEQ ID NO:2, respectively.

Sequences of interest bearing homology to the nucleotide sequences SEQ ID NO:3 and SEQ ID NO:4 include nucleotide sequences encoding SLM-1 or an SLM-1 derivative, and SLM-2 or an SLM-2 derivative, respectively. It will be appreciated by those skilled in the art, that as a result of the degeneracy of the genetic code, a multitude of nucleotide sequences, some bearing minimal nucleotide sequence homology to the nucleotide sequences SEQ ID NO: 3 and SEQ ID NO:4 may be produced. The subject invention includes those polynucleotide sequences which encode the same amino acids using different nucleotides from those specifically exemplified in the sequence listing. Thus, the scope of the subject invention includes not only the specific polynucleotide sequences depicted herein, but also all equivalent polynucleotide sequences encoding the polypeptides of the subject invention, and fragments or variants of the polypeptides having the same activity. For instance, the nucleotide sequence encoding SLM-1 and SLM-2 and their derivatives may be substantially altered without altering the amino acid sequence for the production of RNA transcripts having more desirable properties, e.g., greater half-life, than transcripts produced from the sequences of SEQ ID NO:3 and SEQ ID NO:4.

Nucleotide sequences encoding SLM-1 and SLM-2 and their derivatives may be joined to a variety of other nucleotide sequences of interest by means of well established recombinant DNA techniques (see, for example, Sambrook, et al., Molecular Cloning: A Laboratory Manual, 2nd Ed., Cold Spring Harbor (1989), incorporated herein by reference). Nucleotide sequences of interest for joining include an assortment of vectors, e.g., plasmids, cosmids, lambda phage derivatives, plasmids, and the like, that are in the public domain. Examples of vectors include expression vectors, replication vectors, probe generation vectors, sequencing vectors, and the like. In general, the vectors may contain an origin of replication, functional in at least one organism, convenient restriction endonuclease digestion sites, and selectable markers for the host cell.

Another aspect of the subject invention is to provide for nucleic acid hybridization probes. Uses of such probes include the isolation of SLM-1 or SLM-2, or homologous genes from genomic or cDNA libraries prepared from a variety of cells, in particular mammalian cells. Furthermore, nucleic acid hybridization probes may be used to detect the transcription of SLM-1, SLM-2 or their homologous genes from a variety of organisms by means of northern blots, in situ hybridizations, and the like. Suitable nucleic acid hybridization probes for the detection of SLM-1, SLM-2 and their homologous sequences comprise at least 14, preferably 25, and more preferably at least 500 nucleic acid base pairs from the sequence of SEQ ID NO:3 or SEQ ID NO:4. Hybridization probes may be labelled by a variety of labels including radionuclides, such as $^{32}p$ or $^{35}S$, or enzymatic labels such as alkaline phosphatase coupled to the probe via avidin/biotin coupling systems or the like. An additional use for nucleic acid hybridization probes involves their use as primers for the polymerase chain reaction.

Also of interest is the use of nucleotide sequences of the subject invention for the production of anti-sense oligonucleotides capable of hybridizing to SLM-1 and SLM-2 transcripts. Polynucleotide molecules that are anti-sense to the RNA of SLM-1 or SLM-2 can be prepared using techniques which are known in the art. Antisense oligonucleotides, typically 15 to 20 bases long, bind to the sense mRNA or pre-mRNA region coding for the protein of interest, which can inhibit translation of the bound mRNA to protein. The cDNA sequence encoding SLM-1 or SLM-2 can thus be used to design a series of oligonucleotides which together span a large portion of, or even the entire, cDNA sequence. These oligonucleotides can be tested to determine which provides the greatest inhibitory effect on the expression of the protein. This can be done by exposing cells to the various oligonucleotides and measuring subsequent changes in SLM-1 or SLM-2 biological activity or by using antibodies to screen for inhibition of SLM-1 or SLM-2 synthesis. The most suitable mRNA target sites include 5'- and 3'-untranslated regions as well as the initiation codon. Other regions might be found to be more or less effective. The antisense nucleic acid, polynucleotide or oligonucleotide can be chemically synthesized using naturally occurring nucleotides or variously modified nucleotides designed to increase the biological stability of the molecules or to increase the physical stability of the duplex formed between the antisense and sense polynucleotides, e.g., phosphorothioate derivatives, 2'-O-propyl modified nucleotides and acridine substituted nucleotides can be used.

Anti-sense polynucleotide molecules can be used to reduce or inhibit the expression of the subject protein by binding to the complementary mRNA transcripts, and thus attenuate the expression of SLM-1 and SLM-2 proteins in cells of interest. Anti-sense polynucleotide molecules can be endogenously produced or exogenously added to a cell or cells of interest. Administration of an anti-sense polynucleotide molecule to a patient can block the production of the protein encoded by the SLM-1 or SLM-2 polynucleotide described herein or a related, possibly defective gene.

Likewise, use of anti-gene oligonucleotides, capable of binding through triple helix formation with DNA targets is also contemplated. Such anti-gene oligonucleotides may also be used to attenuate the expression of SLM-1 and SLM-2 proteins in cells of interest.

Salts. Salts of any of the macromolecules described herein will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (such as HCl) of amino residues, and zwitterions formed by reactions between carboxylic acid and amino residues within the same molecule.

Sources of SLM-1 and SLM-2 and their Derivatives. SLM-1, SLM-2, and their derivatives may be purified from a variety of cells such that the indicated molecule is present in the substantial absence of other biological macromolecules, e.g., polypeptides, polynucleic acids, and the like of the same type. The term "purified" as used herein preferably means at least 95% by weight, more preferably at least 99.8% by weight, of biological macromolecules of the same type present (but water, buffers, and other small molecules, especially molecules having a molecular weight of less than 1000 can be present). The term "pure" as used herein preferably has the same numerical limits as "purified" immediately above. The term "isolated" as used herein refers to polypeptide or polynucleotide molecules separated not only from other peptides, DNAs, or RNAs, respectively, that are present in the natural source of the macromolecule but also from other macromolecules and preferably refers to a macromolecule found in the presence of (if anything) only a solvent, buffer, ion or other component normally present in a solution of the same. "Isolated" and "purified" do not encompass either natural materials in their native state or natural materials that have been separated into components (e.g., in an acylamide gel) but not obtained either as pure substances or as solutions.

Suitable cell sources for the production of purified SLM-1, SLM-2 and their derivatives include cells naturally producing SLM-1 and SLM-2, cells not naturally encoding an expressible SLM-1 or SLM-2 gene but genetically modified to do so, and cells naturally producing SLM-1 or SLM-2 but genetically modified so as to produce elevated levels of SLM-1 or SLM-2.

For instance, the polypeptides of the subject invention can be prepared by expression of the polynucleotide sequences in a compatible host cell using an expression vector containing the polynucleotide sequences of the subject invention. The cloning or expression vector may be of bacterial or viral origin. The host cell may be either prokaryotic or eukaryotic and includes bacteria, yeast, insect cells and mammalian cells. Where the host cell is in a transgenic animal, transformation procedures known in the art may be employed, for example, those described in U.S. Pat. Nos. 4,736,866 and 4,870,009, incorporated herein by reference. The polypeptides can then be purified from the host cell using standard purification techniques that are well known in the art.

Preferred cell sources for SLM-1, SLM-2, SLM-1 derivatives, and SLM-2 derivatives produce SLM-1, SLM-2, or their derivatives so that at least 5%, preferably at least 50%, and more preferably at least 90%, of the SLM-1, SLM-2, or their derivatives are phosphorylated. Purification methods for SLM-1, SLM-2, SLM-1 derivatives, and SLM-2 derivatives that depend on affinity reagents specific for phosphotyrosine necessarily employ SLM-1, SLM-2, SLM-1 derivatives, and SLM-2 derivatives isolated from cells that phosphorylate SLM-1, SLM-2, SLM-1 derivatives, and SLM-2 derivatives or from SLM-1, SLM-2, SLM-1 derivatives, and SLM-2 derivatives that have been produced in cells that lack phosphotyrosine activity but have been phosphorylated in vitro with enzymes with tyrosine kinase activity.

Cells from which SLM-1, SLM-2, SLM-1 derivatives, and SLM-2 derivatives may be isolated include both prokaryotic and eukaryotic cells. Preferred cellular sources for the isolation of SLM-1, SLM-2, SLM-1 derivatives, and SLM-2 derivatives include mammalian cells possessing high levels of tyrosine kinase and/or arginine methyltransferase activity. Of particular interest are mammalian cells transfected with tyrosine kinases such as Src, p59fyn, ZAP70, Syk, FAK, JAK and/or arginine methyltransferases such as PRMT1, PRMT2, and PRMT3. Other mammalian cell sources of interest for the purification of SLM-1, SLM-2, SLM-1 derivatives, and SLM-2 derivatives include mammalian cells stimulated by growth factors that bind to growth factor receptors that have tyrosine kinase or arginine methyltransferase activity. Another preferred source for preparations from which to purify SLM-1, SLM-2, SLM-1 derivatives, and SLM-2 derivatives is insect cells, preferably grown in tissue culture, and genetically modified by baculovirus expression vectors or the like to express SLM-1, SLM-2, SLM-1 derivatives, and SLM-2 derivatives and a tyrosine kinase and/or arginine methyltransferase. A particularly preferred source of SLM-1 and SLM-2 derivatives is the SF9 cell line. Another source can be obtained by producing recombinant SLM-1 and SLM-2 in bacteria or yeast as a fusion protein with tags such as histidine repeats or glutathione S-transferase proteins. It will be appreciated that purified SLM-1 and SLM-2 can be phosphorylated or methylated in vitro to yield purified methylated and/or phosphorylated SLM-1 or SLM-2.

Purification of SLM-1, SLM-2 and their Derivatives. Affinity purification of SLM-1, SLM-2, and their derivatives may employ various immobilized reagents specific for SLM-1, SLM-2, or their derivatives, i.e., affinity reagents. The affinity purification may be performed in batches or employ chromatography columns. The affinity reagents may be immobilized to a variety of inert matrices prepared in bead form. Suitable immobilization matrices include cross-linked agarose beads, Sepharose, cross-linked polyacrylamide beads, Sephacryl, and the like. Examples of affinity reagents for purification of SLM-1, SLM-2, and their derivatives include antibodies, purified SH3 domains, purified SH2 domains, and RNA. Purification of phosphorylated SLM-1 or SLM-2 can be performed by using phosphotyrosine specific antibodies and the purification of methylated SLM-1 or SLM-2 can be achieved by using arginine-methylated specific antibodies. Purification of non-phosphorylated SLM-1, SLM-2, and their derivatives may also be achieved through the use of SLM-1 or SLM-2 specific antibodies as affinity reagents.

SLM-1, SLM-2, and their derivatives may be eluted from the immobilized SLM-1 or SLM-2 specific reagents by means of solutions containing molecules that disrupt the interactions between the SLM-1- or SLM-2-specific reagent and SLM-1, SLM-2, or their derivatives; such molecules may be inorganic or organic salts, or may be molecules bearing structural similarity to the region of SLM-1, SLM-2, and their derivatives bound to the SLM-1 and SLM-2-specific affinity reagent.

Other Methods for Obtaining SLM-1, SLM-2, and their derivatives. In addition to production of purified SLM-1, SLM-2, and their derivatives by purification of SLM-1, SLM-2, and their derivatives produced in cells, purified SLM-1, SLM-2, and their derivatives may be produced by organic chemical reactions performed in vitro. Automated equipment for the direct synthesis of polypeptides disclosed herein is commercially available. The use of such commercially available polypeptide synthesis machines and the like are a preferred method of synthesizing oligopeptide SLM-1 and SLM-2 derivatives having about 5–25 amino acids.

Other methods for synthesis of SLM-1, SLM-2, and their derivatives include the in vitro transcription of DNA sequences encoding SLM-1,SLM-2 and their derivatives coupled with the in vitro translation of the RNA transcripts thus produced. In vitro transcription systems are well known in the art. In vitro transcription systems typically involve the creation of nucleotide sequences in which the coding sequence of interest is located downstream from a strong promoter, such as promoters specific for SP-6 or T7 RNA polymerases, followed by the addition of a RNA polymerase specific for the promoter, and substrates required for the reaction. In vitro translation systems are well known in the art and may be used to produce SLM-1, SLM-2, and their derivatives from a variety of transcripts produced by in vitro transcription systems.

SLM-1 and SLM-2 Specific Antibodies. The subject invention also provides for antibodies capable of specifically binding SLM-1 and SLM-2 or SLM-1 and SLM-2 homologous proteins. By the term "antibodies," it is intended both polyclonal and monoclonal antibodies with natural immunoglobulin sequences, synthetic antibody derivatives, and the like; antibodies may be modified so as to be joined to any of a variety of labels, fluorescent, radioactive, enzymatic, biotin/avidin, or the like. Synthetic antibody derivatives include natural immunoglobulin sequences that have been mutated and selected for altered binding specificity, various immunoglobulin gene derived polypeptides, typically single chain, produced by genetically modified bacteria, antibodies modified so as to contain modified constant regions and the like; a review of such synthetic antibody derivatives based on the principles of antibody formation is provided in Harlow and Lane (1988) Antibodies, *A Laboratory Manual*, Cold Spring Harbor Laboratory, Cold Spring Harbor Press, incorporated herein by reference.

Antibodies of interest may be produced by using SLM-1, SLM-2, derivatives thereof, or fragments or peptides thereof, for the induction of specific antibodies. By induction of antibodies it is intended not only the stimulation of an immune response by injection into animals, but analogous steps in the production of synthetic antibodies, such as the screening of recombinant immunoglobulin libraries, Orlandi et al., PNAS USA 86: 3833–3837 (1989) or Huse et al., Science 256: 1275–1281 (1989), both of which are incorporated herein by reference.

SLM-1 and SLM-2 derivatives for use in the induction of antibodies of interest do not need to have SLM-1 or SLM-2 biological activity; however, SLM-1 and SLM-2 derivatives for use in the induction of antibodies will necessarily have immunological activity. Polypeptides for use in the induction of SLM-1 or SLM-2-specific antibodies may have an amino acid sequence consisting of at least five amino acids preferably at least 10 amino acids, mimicking a portion of the amino acid sequence of SLM-1 or SLM-2 and may contain the entire amino acid sequence of SLM-1 or SLM-2.

Short oligopeptides, i.e., containing about 20 amino acids or less, are of particular interest for both the induction and the screening of mono-specific antibodies specific for epitopes of interest. In general, oligopeptides for use in the induction of epitope specific mono-specific antibodies will have an amino acid sequence corresponding to at least a portion of the epitope of interest.

Of particular interest is the production of mono-specific antibodies specific for various epitopes of SLM-1 and SLM-2, such that sets of mono-specific antibodies are developed that are capable of simultaneously binding, i.e., non-overlapping, to different regions of a SLM-1 or SLM-2 molecule. Reasons for the development of sets of simultaneously binding mono-specific antibodies include the production of immunoassays for the detection, quantisation, and measurement of the degree of phosphorylation and/or methylation of SLM-1 and SLM-2. It is also of interest to produce antibody preparations that are capable of specifically binding to a phosphorylated form or a non-phosphorylated form of SLM-1 or SLM-2 but not to both the phosphorylated and non-phosphorylated forms. Likewise, it is of interest to produce antibody preparations that are capable of specifically binding to a methylated form or a non-methylated form of SLM-1 or SLM-2 but not to both the methylated and non-methylated forms.

In one embodiment, the invention provides antibodies specific for SLM-1. Such antibodies may be used in methods of isolating pure SLM-1. In a preferred embodiment, such antibodies do not cross-react with Sam68. In another preferred embodiment, such antibodies do not cross-react with SLM-2. In a further preferred embodiment, such antibodies do not cross-react with SLM-2 nor with Sam68.

In one embodiment, the invention provides antibodies specific for SLM-2. Such antibodies may be used in methods of isolating pure SLM-2. In a preferred embodiment, such antibodies do not cross-react with Sam68. In another preferred embodiment, such antibodies do not cross-react with SLM-1. In a further preferred preferred embodiment, such antibodies do not cross-react with SLM-1 nor with Sam68.

Preferably, specific binding reagents for SLM-1, SLM-2, and their derivatives are produced by the injection of SLM-1 and/or a derivative of SLM-1 with immunological activity, or by the injection of SLM-2 and/or a derivative of SLM-2 with immunological activity, respectively, into mammals for the production of antisera or the production of hybridoma fusion partners. SLM-1, SLM-2, and their derivatives, for the induction of antibody response, are preferably injected into mammals in conjunction with the presence of various adjuvants such as Freund's complete adjuvant, and the like, in order to maximize the immune response to SLM-1, SLM-2, and/or their derivatives.

Antibodies (and antigen binding fragments thereof) raised against the SLM-1 or SLM-2 polypeptides or synthetic peptides thereof are within the scope of the invention. The progress of immunization can be monitored by detection of antibody titers in plasma or serum. Standard ELISA or other immunoassay can be used to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures, thus immortalizing these cells and yielding hybridoma cells. Such techniques are well known in the art. For example, the hybridoma technique originally developed by Kohler and Milstein (Kohler and Milstein, 1975. Nature 256:495–497, incorporated herein by reference) as well as other techniques such as the human B-cell hybridoma technique (Kozbor et al., 1983. Immunol. Today 4:72, incorporated herein by reference), the EBV-hybridoma technique to produce human monoclonal antibodies (Cole et al., 1985. Monoclonal Antibodies in Cancer Therapy. Allen R. Bliss, Inc., incorporated herein by reference), and screening of combinatorial antibody libraries (Huse et al., 1989. Science 246:1275–1281, incorporated herein by reference). Hybridoma cells can be screened immunochemically for production of antibodies specifically reactive with the peptide, and monoclonal antibodies isolated.

The term antibody as used herein is intended to include fragments thereof which are also specifically reactive with a protein having the biological activity of SLM-1 or SLM-2 or a peptide fragment thereof. Antibodies can be fragmented using conventional techniques and the fragments screened for utility in the same manner as described above for whole antibodies. For example, F(ab')$_2$ n fragments can be generated by treating antibody with pepsin. The resulting F(ab')$_2$ fragment can be treated to reduce disulfide bridges to produce Fab' fragments.

It is also known in the art to make chimeric antibody molecules with human constant regions. See, for example, Morrison et al., 1985. Proc. Natl. Acad. Sci. USA 81:6851; Takeda et al., 1985. Nature 314:452; Cabilly et al., U.S. Pat. No. 4,816,567; Boss et al., U.S. Pat. No. 4,816,397; Tanaguchi et al., European Patent Publication EP171496; Teng, et al., 1982. Meth. Enzymol. 92:3–16; European Patent Publication 0173494; United Kingdom Patent GB 2177096B; PCT Publication W092/06193; and EP 0239400, all of which are incorporated herein by reference. It is expected that such chimeric antibodies would be less immunogenic in a human subject than the corresponding non-chimeric antibody. A DNA sequence encoding the entire protein, or a portion of the protein, could thus be linked, for example, with a sequence coding for the C-terminal portion of E. coli β-galactosidase to produce a fusion protein.

Another method of generating specific antibodies, or antibody fragments, reactive against protein having the biological activity of SLM-1, SLM-2 or derivatives and fragments thereof, is to screen expression libraries encoding immunoglobulin genes, or portions thereof, expressed in bacteria, with peptides produced from the nucleic acid molecules of the present invention. For example, complete Fab fragments, VH regions and FV regions can be expressed in bacteria using phage expression libraries. See for example Ward et al., 1989, Nature 341:544–546; Huse et al., 1989, Science 246:1275–1281; and McCafferty et al., 1990., Nature 348, 552–554, all of which are incorporated by reference. Screening such libraries with, for example, SLM-1 or SLM-2 can identify immunoglobulin fragments reactive with SLM-1 or SLM-2. Alternatively, the SCID-hu mouse developed by Genpharm can be used to produce antibodies, or fragments thereof.

The polyclonal, monoclonal or chimeric monoclonal antibodies can be used to detect the proteins of the invention, portions thereof or closely related isoforms in various biological materials, for example they can be used in an ELISA, radioimmunoassay or histochemical tests. Thus, the antibodies can be used to quantify the amount of SLM-1, SLM-2, derivatives thereof, portions thereof or closely related isoforms in a sample in order to determine the role of SLM-1 or SLM-2 in particular cellular events or pathological states. Using methods described hereinbefore, polyclonal antibodies, monoclonal antibodies, or chimeric monoclonal antibodies can be raised to nonconserved regions of SLM-1 or SLM-2 and used to distinguish a particular SLM-1 or SLM-2 from other proteins.

The polyclonal or monoclonal antibodies can be coupled to a detectable substance or reporter system. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}I$; $^{131}I$, $^{35}S$ and $^3H$. In a preferred embodiment, the reporter system allows quantitation of the amount of protein (antigen) present.

Such an antibody-linked reporter system could be used in a method for determining whether a fluid or tissue sample of a subject contains a deficient amount or an excessive amount of the protein. Given a normal threshold concentration of such a protein for a given type of subject, test kits could thus be developed.

The present invention allows the skilled artisan to prepare bispecific antibodies and tetrameric antibody complexes. Bispecific antibodies can be prepared by forming hybrid hybridomas (Staerz & Bevan, 1986, Proc. Natl. Acad. Sci. (USA) 83, 1453; and Staerz & Bevan, 1986, Immunology Today 7:241.v, both of which are incorporated by reference).

Assays. The subject invention provides methods and reagents for performing assays capable of measuring the amount of tyrosine kinase and arginine methyltransferase activity present in a cell and the fraction of SLM-1 or SLM-2 molecules that are phosphorylated and/or methylated.

SLM-1, SLM-2, and their derivatives may be used as substrates for the detection and quantification of tyrosine kinase and arginine methyltransferase activity from a variety of cellular sources. It is desirable to measure tyrosine kinase or arginine methyltransferase activity for several reasons. Of particular interest is the measurement of tyrosine kinase or arginine methyltransferase activity produced by tyrosine kinases or arginine methyltransferase encoded by oncogenes and proto-oncogenes. Thus, assays for tyrosine kinase and/or arginine methyltransferase may be employed to determine whether a cell is cancerous or has cancer potential. Also of interest is the measurement of tyrosine kinase and/or arginine methyltransferase activity attributable to membrane bound ligand receptors with tyrosine kinase and/or arginine methyltransferase activity, since the extent of phosphorylation or methylation of SLM-1 or SLM-2 may be used to measure the extent to which ligands are binding to such receptors.

Tyrosine kinase assays of interest may measure the rate of phosphorylation of SLM-1, SLM-2, or their derivatives by tyrosine kinases in a cell, rather than simply measuring the amount of phosphorylated SLM-1 or SLM-2 present in a cell. Thus tyrosine kinase assays of interest may employ a method for distinguishing tyrosine phosphorylation events that take place during an assay from tyrosine phosphorylation events that occur before an assay. Tyrosine kinase assays may employ the step of adding a phosphate source, preferably ATP and the like, to an assay mixture containing suitable buffers and salts. Phosphate sources may be radioactively labelled on the terminal phosphorous atom, so as to provide for the detection of kinase activity.

Tyrosine kinase activity assays employing radioactive labels may or may not employ the step of addition of SLM-1, SLM-2 or their derivatives, because tyrosine kinase substrates initially present in the cell or SLM-1, SLM-2, or their derivatives added externally, and subsequently phosphorylated by the radioactive phosphate source, may subsequently be isolated by addition of SLM-1 or SLM-2-specific antibodies, followed by the step of radiometric quantisation. Generally, it will be preferable to add SLM-1 or SLM-2, preferably produced by recombinant means, to the assay mixture. After the kinase reaction has been allowed to progress, the amount of radioactive label incorporated into SLM-1 is measured by radiometric means. In order to measure the amount of labelling, the unincorporated label must be removed prior to radiometric measurement. This removal can be achieved through a variety of means including immunoprecipitation of SLM-1 with anti-SLM-1 antibodies.

An important advantage of the subject invention is that the polypeptides provided for permit the detection and quantification of tyrosine kinase activity without requiring the addition of radioactively labelled phosphates. The absence of a need for a radionuclide label improves the safety and lowers the cost of performing assays. Methods for measuring tyrosine kinase activity without the addition of radioactively labelled phosphates include assays involving the use of (1) SLM-1 or SLM-2 derivatives that contain epitopes not present on SLM-1 or SLM-2, (2) antibodies specific for that epitope, (3) antiphosphotyrosine antibodies or SH2 domain containing proteins. Such assays involve the addition of the SLM-1 or SLM-2 derivatives to the assay mixture, followed by the immunoprecipitation or immobilization of the SLM-1 or SLM-2 derivative by means of the epitope specific antibody so as to separate the SLM-1 or SLM-2 derivative from other cellular proteins containing phosphorylated tyrosine (including endogenous SLM-1 and SLM-2); the amount of phosphorylated SLM-1 or SLM-2 derivative complexed with the epitope specific antibody may then be measured by binding with phosphotyrosine-specific antibodies or SH2 domain containing proteins such as Src kinases, Grb2, p120ras GAP or PLCg1.

In addition to providing methods and reagents for use in the detection of tyrosine kinase activity present in a cell, the subject invention provides methods and reagents for determining what fraction of the SLM-1 or SLM-2 in a cell is phosphorylated as well as determining the absolute amount of phosphorylated SLM-1 or SLM-2 present in a cell. Tyrosine phosphorylation of SLM-1 or SLM-2 may be detected by a variety of means. If the phosphate source in the assay contains a radioactive label, then tyrosine kinase activity may be detected by separating the labelled SLM-1 or SLM-2 from the unincorporated label and quantifying the amount of label incorporated into the SLM-1 or SLM-2 substrate. When non-radioactively labelled phosphate sources are used in assays, phosphorylated SLM-1 or SLM-2 may be detected by means of generally known immunoassays in which the immunospecific reagent employed is specific for phosphotyrosine.

The subject invention provides for methods and reagents for performing assays capable of determining what fraction of SLM-1 or SLM-2 in a cell is phosphorylated. Such assays may employ well known immunoassay technology such as ELISA, RIA, western blotting, and the like. The use of SLM-1 or SLM-2 specific antibodies (as well as SLM-1, SLM-2, and their derivatives) as provided for by the subject invention may be used in connection with the previously described well-established immunoassay technology in order to provide for assays capable of detecting the extent of SLM-1 or SLM-2 phosphorylation in a cell. In general, such assays will employ two types of SLM-1- and SLM-2-specific antibodies (or similar binding reagent) in an immobilized phase: (1) antibodies capable of binding SLM-1 or SLM-2 in both phosphorylated and non-phosphorylated form or antibodies capable of binding only the non-phosphorylated form of SLM-1 or SLM-2, and (2) antibodies capable of binding the phosphorylated SLM-1 or SLM-2, or SH2 domain containing proteins such as Src kinases, Grb2, p120ras GAP or PLCg1 derivatives that have similar specificity for the phosphorylated form of SLM-1 or SLM-2. By employing two types of specific binding reagent, it is possible to determine the relative quantities of the phosphorylated and non-phosphorylated forms of SLM-1 or SLM-2 present in a sample. The binding of SLM-1 or SLM-2 (phosphorylated and non-phosphorylated) to an immobilized antibody phase may be detected by the addition of a third antibody, preferably labelled, and having an affinity for exposed epitopes on the antibody bound SLM-1 or SLM-2. Comparison of binding of the labelled antibody to SLM-1- or SLM-2-bound to the 2 different types of immobilized antibody may be used to determine the fraction of phosphorylated SLM-1 or SLM-2 present among the total SLM-1 or SLM-2 present in the sample.

Detection of Cancerous Cells. SLM-1 and SLM-2 specific antibodies may also find use in the labelling of cells for use in techniques such as FACS, in situ immunohistological staining, and the like. SLM-1 and SLM-2 specific antibodies for use in such techniques are labelled, either directly or indirectly. The labelling of cells with SLM-1- or SLM-2-specific antibodies, especially antibodies specific for phosphorylated SLM-1 or SLM-2, find numerous uses including the detection of cancerous cells, pre-cancerous cells, and cells stimulated by various growth factors.

Transgenic non-human mammals. The present invention relates to transgenic non-human mammals, at least some cells of which include a recombinant expression vector that comprises a nucleic acid sequence encoding SLM-1, SLM-2, or their derivatives. Preferably, such nucleic acid sequence encodes the amino acid sequence of SEQ ID NO:1 or SEQ ID NO:2. Transgenic non-human mammals useful for producing recombinant proteins are well known as are expression vectors and techniques used for generating transgenic animals. For example, cells of the transgenic animal include a recombinant expression vector in which the nucleotide sequence that encodes the invention is operably linked to a mammary cell specific promoter whereby the coding sequence is only expressed in mammary cells and the recombinant protein so expressed is recovered from the animal's milk. In some embodiments, the coding sequence that encodes an SLM-1 or SLM-2 is SEQ ID NO:3 or SEQ ID NO:4.

In another embodiment, the present invention relates to knockout animals and methods of using the same. In particular, transgenic mice may be generated which are homozygous for either a mutated, non-functional SLM-1 or SLM-2 gene which is introduced into the mice using well known techniques. The mice produce no functional SLM-1 or SLM-2 and are useful for studying the function of SLM-1 or SLM-2. Furthermore, the mice may be used in assays to study the effect of test compounds on SLM-1 or SLM-2 deficiency.

Methods of generating genetically deficient "knockout" mice are well known and disclosed in Capecchi, M. R., Science, 1989, 244, 1288–1292 and Li, P., et al., Cell, 1995, 80, 401–411, which are each incorporated herein by reference. The murine SLM-1 and SLM-2 genomic clone can be used to prepare a SLM-1 or SLM-2 targeting construct which can disrupt the SLM-1 or SLM-2 gene in the mouse by homologous recombination.

Other Uses. The molecules of the subject invention can also be used in gene therapy protocols. For example, the polynucleotide sequences of the present invention can be incorporated into vectors that are suitable for delivering the subject polynucleotide sequences into the cells of a patient afflicted by a given disease. The sequences are inserted and expressed in the patient's cells such that the patient's transformed cells will produce the polypeptide encoded by the polynucleotide sequence.

The polynucleotide sequences of the subject invention can also be used in antisense gene therapy protocols. For antisense therapy, a polynucleotide sequence of the present invention is selected which encodes an anti- sense polynucleotide strand, typically RNA, which is capable of binding to an RNA sense strand. Antisense therapy is directed to preventing the production of defective proteins in the patient's cells through the annealing of an anti-sense strand to the RNA sense strand. Gene therapy protocols are known to those skilled in the art.

Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotide thereof, can be directly introduced into tissues in vivo, using delivery vehicles such as liposomes, retroviral vectors, adenoviral vectors and DNA virus vectors. A delivery vehicle can be chosen which can be targeted to a cell of interest in the subject. Antisense nucleic acids can also be introduced into isolated cells, ex vivo using viral vectors, or physical techniques such as microinjection and electroporation, or chemical methods such as coprecipitation and incorporation of DNA into liposomes, and such cells can be returned to the donor. Recombinant molecules can be delivered in the form of an aerosol or by lavage.

The nucleic acids of the invention can further be used to design ribozymes which are capable of cleaving a single-stranded nucleic acid encoding SLM-1 or SLM-2, such as an mRNA. A catalytic RNA (ribozyme) having ribonuclease activity can be designed which has specificity for a SLM-1 or SLM-2 encoding mRNA based upon the sequence of a nucleic acid of the invention. Alternatively, a nucleic acid of the invention could be used to select a catalytic RNA having a specific ribonuclease activity from a pool of RNA molecules.

The isolated nucleic acids and antisense nucleic acids of the invention can be used to construct recombinant expression vectors as described previously. These recombinant expression vectors are then useful for making transformant host cells containing the recombinant expression vectors, for example, for expression of protein encoded by the nucleic acids of the invention, and for isolating proteins of the invention as described previously. The isolated nucleic acids and antisense nucleic acids of the invention can also be used to construct transgenic and knockout animals as described herein.

The following examples are provided in order to illustrate the methods of the present invention and are not meant to limit the scope of the invention.

EXAMPLES

The identification and cloning of SLM-1 and SLM-2. The public expressed sequence tag (EST) database was searched with the BLAST program (Altschul, S. F., Gish, W., Miller, W., Myers, E. W., & Lipman, D. J. (1990) *J. Mol. Biol.* 215, 403–410, incorporated herein by reference) using the Sam68 amino acid sequence. The human EST 530290 was identified as a family member of Sam68. The cDNA encoding SLM-1 and SLM-2 were obtained by screening a λ ZAP II mouse brain library (Stratagene, La Jolla, Calif.) with a $^{32}$p random-primed DNA fragment encompassing the entire insert of the human EST clone 530290 (GenBank accession AA083787). Clone 18-2 had an insert of 1.9 kb in length and was the mouse 530290 cDNA. Seventeen other clones were obtained that were shorter than clone 18-2. Two other clones were obtained that were not identical to 530290. Clone 6-1 was a mouse Sam68 partial cDNA and clone 1-1 had an insert of 1.3 kb with features of both Sam68 and 530290. The proteins encoded by clones 1-1 and 18-2 were similar to Sam68, and were named SLM-1 and SLM-2, respectively, for Sam68 like mammalian proteins. Clone 1-1 contained the entire SLM-1 coding sequence and the full-length SLM-1 DNA sequence of 2.4 kb was obtained by sequencing several overlapping clones obtained by using clone 1-1 as a probe on a mouse brain λ ZAP II library. The cDNAs were sequenced on both strands with multiple overlapping reads using an automated ABI sequencer.

DNA constructs. Myc epitope tagged SLM-1 and SLM-2 were generated by subcloning the EcoRI DNA fragment of clones 1-1 and 18-2 into myc-Bluescript KS, respectively (Richard, S., Yu, D., Blumer, K. J., Hausladen, D., Olszowy, M. W., Connelly, P. A., & Shaw, A. S. (1995) *Mol. Cell. Biol.* 15, 186–197, incorporated herein by reference). GFP- SLM-1 and GFP-SLM-2 were generated by subcloning the EcoRI DNA fragment of clones 1-1 and 18-2 into pEGFP-C1. GFP-Sam68 was constructed by subcloning the EcoRI fragment of myc-Sam68f (Richard, S., Yu, D., Blumer, K. J., Hausladen, D., Olszowy, M. W., Connelly, P. A., & Shaw, A. S. (1995) *Mol. Cell. Biol.* 15, 186–197, incorporated herein by reference) into pEGFP-C1. Bluescript-fyn, myc-Sam68, HA-Sam68, and the plasmids encoding the SH3 and SH2 domains of $p59^{fyn}$, PLCγ1, $p120^{ras-GAP}$ and Grb-2 are as described previously (Richard, S., Yu, D., Blumer, K. J., Hausladen, D., Olszowy, M. W., Connelly, P. A., & Shaw, A. S. (1995) Mol. Cell. Biol. 15, 186–197 and Chen, T., Damaj, B., Herrerra, C., Lasko, P., & Richard, S. (1997) *Mol. Cell. Biol.* 17, 5707–5718, both of which are incorporated by reference). The purified glutathione S transferase (GST) fusion proteins were covalently coupled to Affi-Gel 10 (Bio-Rad) at concentrations of 2 mg/ml. The plasmid constructs were verified by dideoxynucleotide sequencing with Sequenase (U.S. Biochemical).

Northern blot analysis. Northern blot analyses were performed to examine the tissue distribution of SLM-1 and SLM-2 transcripts. The mouse and human multiple tissue Northern blot membranes were purchased from Clontech (Palo Alto, Calif.). A $^{32}P$ random-primed DNA fragment containing the entire insert of SLM-1 (clone-1-1) or SLM-2 (clone 18-2) was used to hybridize the membrane according to the manufacturer's protocol using the ExpressHyb™ solution for 1 h at 68° C. The mouse SLM-1 gene encodes several transcripts including a 2.2 kb mRNA expressed in the heart, brain, spleen, kidney, and testis. A transcript of 2.4 kb was also observed in the brain and a smaller transcript was observed in the testis that may represent alternatively spliced SLM-1 variants. For SLM-2, a ubiquitous transcript of 2.5 kb was observed that was most abundant in the brain and skeletal muscle. An additional transcript of ~3.3 kb was also observed in brain and skeletal muscle. Thus, SLM-1 transcript is ubiquitously expressed while the expression of SLM-2 transcript is more restricted with high levels in the brain and skeletal muscle.

Protein expression and protein analysis. The Applicant expressed SLM-1 and SLM-2 in HeLa cells with an N-terminal myc epitope sequence recognized by the monoclonal antibody 9E10 (Evan, G. I., & Bishop, J. M. (1985) *Mol. Cell. Biol.* 4, 2843–2850, incorporated herein by reference). The vaccinia virus T7 expression system (Richard, S., Yu, D., Blumer, K. J., Hausladen, D., Olszowy, M. W., Connelly, P. A., & Shaw, A. S. (1995) *Mol. Cell. Biol.* 15, 186–197, incorporated herein by reference) was used. Immunoblotting and/or immunoprecipitations were performed using anti-myc 9E10, anti-hemagglutinin (HA), anti-phosphotyrosine mixture containing 1:1000 PY20 and 1:2000 4G10 anti-phosphotyrosine antibodies, and anti-$p59^{fyn}$ antibodies. The Applicant has shown in previous studies that an N-terminal myc epitope tag does not interfere with signaling and RNA binding properties (Richard, S., Yu, D., Blumer, K. J., Hausladen, D., Olszowy, M. W., Connelly, P. A., & Shaw, A. S. (1995) *Mol. Cell. Biol.* 15, 186–197; Chen, T., Damaj, B., Herrerra, C., Lasko, P., & Richard, S. (1997) *Mol. Cell. Biol.* 17, 5707–5718; and Wang, L. L., Richard, S., & Shaw, A. S. (1995) J. Biol. Chem. 270, 2010–2013, all of which are incorporated herein by reference). The plasmids expressing myc-SLM-1 and myc-SLM-2 were transfected in HeLa cells and cell lysates expressing these proteins were separated by SDS-PAGE and immunoblotted with anti-myc antibodies. Myc-SLM-1 protein migrated at ~64 kDa and myc-SLM-2 migrated at ~68 kDa. The amino acid composition of SLM-1 (349 amino acids) and SLM-2 (346 amino acids) predict molecular masses in the 35 to 45 kDa range. The aberrant migration of SLM-1 and SLM-2 on SDS polyacrylamide gels is likely due to the presence of highly negatively charged C-termini. SLM-1 and SLM-2 contain 16 tyrosines in their C-termini. The Applicant examined whether SLM-1 and SLM-2 were substrates of the $p59^{fyn}$. SLM-1 and SLM-2 were co-expressed with $p59^{fyn}$ in HeLa cells, the cells were lysed and immunoprecipitated with control (IgG) or anti-myc antibodies. The bound proteins were separated by SDS-PAGE and immunoblotted with anti-phosphotyrosine antibodies. SLM-1 was readily tyrosine phosphorylated. Surprisingly, SLM-2 was not tyrosine phosphorylated by $p59^{fyn}$.

Assessing the bind to SH3 and SH2 domain containing proteins. SLM-1 contains four proline motifs named P1 to P4 and SLM-2 contains only one. Proline motifs that serve as SH3 domain binding sites have been classed as class I (RxxPxxP) and class II (PxxPxR). SLM-1 P1 (RITPTAP) (SEQ. ID. NO 5) is the only proline motif that is in class I configuration. SLM-1 P2 (PPPPPPGR) (SEQ. ID. NO. 6) is in a class II configuration. P3 (RGALPVPPI) (SEQ. ID. NO. 7) and P4 (RAPPPPA) (SEQ. ID. NO. 8) are not in a class I or class II configuration. The SLM-2 proline motif (RPPPPPPT) (SEQ. ID. NO. 9) is in a class I configuration. The SH3 and SH2 domain specificity of SLM-1 and SLM-2 was compared to that of Sam68 by performing gluthione-s-transferase (GST) 'pull-down' assays. v-Src transformed cells were plated 12 h before transfection typically at a density of $10^5$ cells/35 mm well. Cells were transfected with DNA constructs encoding GFP alone, GFP-Sam68. GFP-SLM-1, and GFP-SLM-2 using LipofectAMINE PLUS reagent (Life Technologies, Inc.). 8 h after transfection, nocodazole was added to make a final concentration of 40 ng/ml and incubated overnight. Prior to harvesting, cells were treated with pervanadate for 15 min and lysed as described above. HeLa cells were transfected with myc-Sam68, myc-SLM-1 or myc-SLM-2, the cells were lysed, divided equally and incubated with GST alone, GST-fynSH3, GST-PLCγ-1SH3 and GST-GAPSH3 fusion proteins covalently coupled to beads. SLM-1 bound the SH3 domain of $p59^{fyn}$, PLCγ-1, but with lower relative affinities than Sam68. SLM-2 did not associate with the SH3 domains of $p59^{fyn}$, PLCγ-1 and $p120^{rasGAP}$.

The Applicant investigated whether tyrosine phosphorylated SLM-1 could bind the SH2 domains of $p59^{fyn}$, PLCγ-1, $p120^{rasGAP}$ and Grb2. HeLa cells were co-transfected with $p59^{fyn}$ and myc-Sam68, myc-SLM-1 or myc-SLM-2. The cells were lysed, divided equally and incubated with GST alone, GST-fynSH2, GST-PLCγ-1SH2/SH2, GST-GAPSH2/SH3/SH2 and GST-Grb2SH2 fusion proteins covalently coupled to beads. The bound myc epitope tagged proteins were detected by immunoblotting with anti-myc antibodies. Tyrosine phosphorylated SLM-1 bound the SH2 domains of $p59^{fyn}$, PLCγ-1, $p120^{rasGAP}$ and Grb2 in vitro. Since SLM-2 was not phosphorylated by $p59^{fyn}$, it was unable to associate with any SH2 domain containing proteins. The presence of similar tyrosine motifs in SLM-2 suggests that once tyrosine phosphorylated, it should bind the same SH2 domain containing proteins.

SEQUENCE LISTING

<160> NUMBER OF SEQ ID NOS: 9

<210> SEQ ID NO 1
<211> LENGTH: 349
<212> TYPE: PRT
<213> ORGANISM: Mus musculus

<400> SEQUENCE: 1

```
Met Gly Glu Glu Lys Tyr Leu Pro Leu Met Ala Glu Lys Asp Ser
 1               5                  10                  15

Leu Asp Pro Ser Phe Val His Ala Ser Arg Leu Leu Ala Glu Glu Ile
                20                  25                  30

Glu Lys Phe Gln Gly Ser Asp Gly Lys Lys Glu Asp Glu Lys Lys
             35                  40                  45

Tyr Leu Asp Val Ile Ser Asn Lys Asn Ile Lys Leu Ser Glu Arg Val
     50                  55                  60

Leu Ile Pro Val Lys Gln Tyr Pro Lys Phe Asn Phe Val Gly Lys Leu
 65                  70                  75                  80

Leu Gly Pro Arg Gly Asn Ser Leu Lys Arg Leu Gln Glu Glu Thr Gly
                 85                  90                  95

Ala Lys Met Ser Ile Leu Gly Lys Gly Ser Met Arg Asp Lys Thr Lys
                100                 105                 110

Glu Glu Glu Leu Arg Lys Ser Gly Glu Ala Lys Tyr Ala His Leu Ser
            115                 120                 125

Asp Glu Leu His Val Leu Ile Glu Val Phe Ala Pro Pro Gly Glu Ala
            130                 135                 140

Tyr Ser Arg Met Ser His Ala Leu Glu Glu Ile Lys Lys Phe Leu Val
145                 150                 155                 160

Pro Asp Tyr Asn Asp Glu Ile Arg Gln Glu Gln Leu Arg Glu Leu Ser
                165                 170                 175

Tyr Leu Asn Gly Ser Glu Glu Ser Gly Arg Gly Arg Gly Ile Arg Gly
                180                 185                 190

Arg Gly Ile Arg Ile Thr Pro Thr Ala Pro Ser Arg Gly Arg Gly Gly
            195                 200                 205

Ala Val Pro Pro Pro Pro Pro Gly Arg Gly Val Leu Thr Pro Arg
    210                 215                 220

Gly Thr Thr Val Thr Arg Gly Ala Leu Pro Val Pro Ile Ala Arg
225                 230                 235                 240

Gly Val Pro Thr Pro Arg Ala Arg Gly Thr Ala Ala Val Pro Gly Tyr
                245                 250                 255

Arg Ala Pro Pro Pro Ala His Asp Ala Tyr Glu Glu Tyr Gly Tyr
            260                 265                 270

Asp Asp Gly Tyr Gly Glu Tyr Asp Asp Gln Thr Tyr Glu Ala Tyr
            275                 280                 285

Asp Asn Ser Tyr Val Thr Pro Thr Gln Ser Val Pro Glu Tyr Tyr Asp
    290                 295                 300

Tyr Gly His Gly Val Asn Glu Asp Ala Tyr Asp Ser Tyr Ala Pro Glu
305                 310                 315                 320

Glu Trp Ala Thr Thr Arg Ser Ser Leu Lys Ala Pro Pro Pro Arg Ser
                325                 330                 335

Ala Arg Gly Gly Tyr Arg Glu His Pro Tyr Gly Arg Tyr
            340                 345
```

-continued

```
<210> SEQ ID NO 2
<211> LENGTH: 346
<212> TYPE: PRT
<213> ORGANISM: Mus musculus

<400> SEQUENCE: 2

Met Glu Glu Lys Tyr Leu Pro Glu Leu Met Ala Glu Lys Asp Ser Leu
 1               5                  10                  15

Asp Pro Ser Phe Thr His Ala Leu Arg Leu Val Asn Arg Glu Ile Glu
            20                  25                  30

Lys Phe Gln Lys Gly Glu Gly Lys Glu Glu Lys Tyr Ile Asp Val
        35                  40                  45

Val Ile Asn Lys Asn Met Lys Leu Gly Gln Lys Val Leu Ile Pro Val
 50                  55                  60

Lys Gln Phe Pro Lys Phe Asn Phe Val Gly Lys Leu Leu Gly Pro Arg
65                  70                  75                  80

Gly Asn Ser Leu Lys Arg Leu Gln Glu Thr Leu Thr Lys Met Ser
                85                  90                  95

Ile Leu Gly Lys Gly Ser Met Arg Asp Lys Ala Lys Glu Glu Leu
                100                 105                 110

Arg Lys Ser Gly Glu Ala Lys Tyr Phe His Leu Asn Asp Asp Leu His
        115                 120                 125

Val Leu Ile Glu Val Phe Ala Pro Pro Ala Glu Ala Tyr Ala Arg Met
130                 135                 140

Gly His Ala Leu Glu Glu Ile Lys Lys Phe Leu Ile Pro Asp Tyr Asn
145                 150                 155                 160

Asp Glu Ile Arg Gln Ala Gln Leu Gln Glu Leu Thr Tyr Leu Asn Gly
                165                 170                 175

Gly Ser Glu Asn Ala Asp Val Pro Val Val Arg Gly Lys Ser Thr Leu
            180                 185                 190

Arg Thr Arg Gly Val Thr Thr Pro Ala Ile Thr Arg Gly Arg Gly Gly
        195                 200                 205

Val Thr Ala Arg Pro Val Ala Val Gly Val Pro Arg Gly Thr Pro Thr
210                 215                 220

Pro Arg Gly Val Leu Ser Thr Arg Gly Pro Val Ser Arg Gly Arg Gly
225                 230                 235                 240

Leu Leu Thr Pro Arg Ala Arg Gly Val Pro Pro Thr Gly Tyr Arg Pro
                245                 250                 255

Pro Pro Pro Pro Thr Gln Glu Thr Tyr Gly Glu Tyr Asp Tyr Asp
            260                 265                 270

Asp Gly Tyr Gly Thr Ala Tyr Asp Glu Gln Ser Tyr Asp Ser Tyr Asp
        275                 280                 285

Asn Ser Tyr Ser Thr Pro Ala Gln Ser Ala Ala Asp Tyr Tyr Asp Tyr
290                 295                 300

Gly His Gly Leu Ser Glu Asp Ala Tyr Asp Ser Tyr Gly Gln Glu Glu
305                 310                 315                 320

Trp Thr Asn Ser Arg His Lys Ala Pro Ser Ala Arg Thr Ala Lys Gly
                325                 330                 335

Val Tyr Arg Asp Gln Pro Tyr Gly Arg Tyr
            340                 345

<210> SEQ ID NO 3
<211> LENGTH: 2368
<212> TYPE: DNA
<213> ORGANISM: Mus musculus
```

<400> SEQUENCE: 3

```
ttttttttgag tccttccaat atttattata gtgggtcaga agcagcaaga gagccagagg      60
gacaggaacc cagattattt gttcttcagg tagatcttcg gggtctgcca gttctcaggg     120
gcttccttca ggcctgcctt aagccagatg cgcttcaagt cttctcaaa tttgatctgc      180
ttcttcttca aacgtcctcc ccggaccttg cgacgtagaa accgggtcct tttgaccagt     240
ttacggtact tgtggtggtt catctttcgc cttcggatct tcagcacgtt tgcactgcac     300
tggagtggca tcccaggctt ccctgactcc ctgctgggct tcctcctccc cctgcctagg     360
tggacattcg tagaactggg agggagccag agtcactggg acctcgacat tccgtctggg     420
caataagtat tgagcagtca gccagctctc tagaggactg atggccatct tcctggggac     480
caggaactcc tcaagctctg actgggtcct cttaccaggg agggaggcag cccgacttgg     540
gcttgcaggc tgcaaactgt aaaggggtcg aaaagcatag ctgccaatca ccccggagcc     600
agggcaggaa cgactgaaac ctgcccaggg aacaacagtc ctggccagcc gtgaagtcag     660
gcgcgccagg aacatggtga gcagttggtc cggcggcagc gctcaaagct agaacacagg     720
aaccagctga ggtcacgcag cggcgacggg cagtgctctc ggccgcaggc ctcgcatatc     780
ccatcaccct ggtcccctg acccgcgata aggagacatc ttcaaaagtc gctctgagcg      840
caaatcctgt ccatacttct ctccaccagc gtggtcgctg taagccgccc acccacggtt     900
cccgctcagg cagcgaaacc cacagcgcag gacgatatcg acgctcgcac gcaccaaaca     960
gacgcaggcc aagcgagctc cgcctcgtgc cgaattcggc acgagggcgc tagagctgcg    1020
ctctacggtg gaagaacggt tcccggggga gccagggacc aaggcgtcgg agcgggcgga    1080
aattgcgcct gaccgggcac ggtccgaagt ccgcgctatg ggagaagaga aatacttgcc    1140
tgagctgatg gcagagaagg atagcctgga tccatctttt gtgcacgcgt cgcgccttct    1200
ggcggaagaa attgagaaat tcaaggttc agatgggaaa aaggaagatg aagaaaagaa     1260
atatctcgat gtcatcagca acaaaaacat aaagctctct gaaagagtat tgattcctgt    1320
gaaacagtat ccaaagttca attttgtggg gaaattgctt ggaccaagag gaaactcctt    1380
gaagaggcta caagaagaaa cgggtgctaa aatgtctatc ctgggcaaag ggtccatgcg    1440
agataagaca aaggaagaag agctgaggaa gagtggggag gccaagtatg cccacctgag    1500
tgatgagctg catgtattaa ttgaagtgtt tgctccaccc ggggaagctt attcacggat    1560
gagtcatgcc ttggaagaga ttaaaaaatt cctggttcct gactacaatg atgaaattcg    1620
tcaagagcaa ctccgggagt tgtcttactt gaatggctca gaagagtctg gccggggccg    1680
aggtattaga ggcagaggga tcagaataac tcccacagct ccatcaaggg gccgtggcgg    1740
tgctgttcca ccaccaccac cacctggacg aggtgtgctt accccctcggg ggaccactgt   1800
gacccgtgga gctcttccag tgcccccaat agcaagaggt gtcccacac ctcgagcccg     1860
ggggacggca gcagtaccag gatacagagc acccccacct ccagctcatg atgcttatga    1920
agaatatggg tatgatgatg ctatggggg tgaatatgat gaccagacct atgaggctta     1980
tgataatagc tacgtgaccc caacacaaag tgtgcctgaa tactatgact acggtcatgg    2040
agtaaacgag gatgcctacg acagctacg accagaagaa tgggccacaa ctcgctccag     2100
cctgaaggca ccaccaccaa ggtcagccag agggggatac agggagcacc cctatggtag    2160
atattgaagg tcctcttcat ctgtgacctc ctcaaagaca attcatagcc tgtggtctcc    2220
acataaacag caacaagaca agtaatagtc ctttttttgt ttgtttgttt tttctgttct    2280
aggaataact gctcataatt gctcccacta tttcttgtat tcccttatac tgttaatgtg    2340
```

-continued acgtggacat tagtattatt ttaccctg                                              2368

<210> SEQ ID NO 4
<211> LENGTH: 1896
<212> TYPE: DNA
<213> ORGANISM: Mus musculus

<400> SEQUENCE: 4

| aagcgcgggg | cgggtcgtgg | cagagcaagg | catcgaggtc | gcagccggcg | agcaagactg |   60 |
| gccagcgctc | ctcggctttc | cagcccgctc | tcttcgctca | tcccgccgcc | ttgcagcccg |  120 |
| cggcccgcag | cgcggtgatc | tggggctcca | cggggccggg | ctgagcggcc | gccgcccgcc |  180 |
| ccgagccgcc | gccgccgccc | ggccgccgc  | ccggcttagc | cgccgaggcg | cctggcgggt |  240 |
| tccgcgccgc | cggggcgggc | cggctcgggc | tgcggggcgg | ctggcgcgcg | cgcgccgcgg |  300 |
| gcggccggcg | gagaagcggg | cccggcgcc  | ggcgagcatg | gaggagaagt | acctgccgga |  360 |
| gctgatggcg | gagaaggact | ctctggaccc | ctccttcacg | cacgccctgc | gcttggtgaa |  420 |
| ccgagaaata | gaaaagtttc | aaaagggaga | aggcaaggag | gaagagaagt | acattgacgt |  480 |
| ggtgataaac | aagaacatga | gctgggaca  | gaaggtgctg | attcccgtga | agcagtttcc |  540 |
| caagttcaac | tttgtgggga | gcttttggg  | tccgcgtggc | aattccctga | agcgcttaca |  600 |
| agaagaaacg | ttgacaaaaa | tgtccatcct | tggcaaaggt | tccatgagag | acaaggcaaa |  660 |
| ggaggaagag | ctgaggaaaa | gtggagaagc | gaagtacttt | cacctcaatg | acgacctgca |  720 |
| cgtgctcatt | gaagtgttcg | cacccccagc | agaagcatat | gcccggatgg | ggcacgcctt |  780 |
| ggaagagatc | aagaaattcc | tgatccctga | ctataatgat | gaaatcaggc | aagcacaact |  840 |
| ccaggagtta | acatatttga | atggaggttc | agaaaatgca | gatgtcccag | tggttcgagg |  900 |
| gaaatctact | ttgcgtacga | gaggtgtaac | tacaccagca | ataaccaggg | gaagaggagg |  960 |
| agtcacagcc | aggcctgttg | cagttgggt  | accacgtggg | acaccgactc | cccgaggagt | 1020 |
| cctttccacc | cgagggccag | tgagccgggg | aagaggcctt | ctcactccca | gagcaagagg | 1080 |
| tgtccccccca | accggataca | gacctccccc | gccacccca  | acacaggaga | cctatggaga | 1140 |
| gtatgactat | gacgatgggt | acggtactgc | ctatgatgag | cagagctatg | actcctatga | 1200 |
| caacagctac | agcaccccag | cacaaagtgc | agctgattac | tacgattatg | ggcatggact | 1260 |
| cagcgaggac | gcttatgact | cctatgggca | agaggaatgg | actaactcaa | gacataaggc | 1320 |
| tccttcggcg | aggacggcga | agggcgtcta | cagagaccag | ccatatggca | gatactgatt | 1380 |
| gtactgtctg | atgttgtgaa | atagccaatc | tccaccgtcc | tgtatactgt | tcaaagtaat | 1440 |
| ttttttctat | gaccaatccc | tttttaaata | aatcaaaatg | cttaaaatct | gaatggatgg | 1500 |
| aacttaaagc | cactttgttg | aagcatccac | ttgacaggga | gaagaargac | atgtaaaatt | 1560 |
| ttgttatttg | cagtctgtat | atgaaaacta | ggttatgaaa | aggaaaaaaa | taactttgat | 1620 |
| taactagtgt | taaacaaaaa | gataggttta | ctaaatatgt | taatccattc | tttaacataa | 1680 |
| gtctcacctt | tcatcttaaa | ggtttccata | gaatttagtt | attttatctt | tcagccatat | 1740 |
| gctagttttt | tttttcttct | ttctttcttg | ccaacttgcg | taaaaaggga | gccgattaca | 1800 |
| agtgcagaca | atgtggtatt | cttttgtaac | tgagtcctga | aatgttctgt | agtgttaggc | 1860 |
| aaagtctcct | cttgcttgat | actaaataaa | cttttg     |            |            | 1896 |

<210> SEQ ID NO 5
<211> LENGTH: 7
<212> TYPE: PRT

```
<213> ORGANISM: Mus musculus

<400> SEQUENCE: 5

Arg Ile Thr Pro Thr Ala Pro
 1               5

<210> SEQ ID NO 6
<211> LENGTH: 8
<212> TYPE: PRT
<213> ORGANISM: Mus musculus

<400> SEQUENCE: 6

Pro Pro Pro Pro Pro Gly Arg
 1               5

<210> SEQ ID NO 7
<211> LENGTH: 9
<212> TYPE: PRT
<213> ORGANISM: Mus musculus

<400> SEQUENCE: 7

Arg Gly Ala Leu Pro Val Pro Pro Ile
 1               5

<210> SEQ ID NO 8
<211> LENGTH: 6
<212> TYPE: PRT
<213> ORGANISM: Mus musculus

<400> SEQUENCE: 8

Arg Ala Pro Pro Pro Ala
 1               5

<210> SEQ ID NO 9
<211> LENGTH: 8
<212> TYPE: PRT
<213> ORGANISM: Mus musculus

<400> SEQUENCE: 9

Arg Pro Pro Pro Pro Pro Thr
 1               5
```

The embodiments of the invention in which an exclusive property or privilege is claimed are defined as follows:

1. An isolated polypeptide comprising at least 25 consecutive amino acids of SEQ ID NO. 1, wherein the polypeptide contains at least 2 proline motifs, can act as a substrate for a tyrosine kinase, and can act as a substrate for arginine methyltransferase.

2. A polypeptide according to claim 1, comprising SEQ ID NO. 1.

3. A polypeptide encoded by a DNA comprising the nucleic acid sequence of SEQ ID NO. 3 wherein the polypeptide contains at least two proline motifs, can act as a substrate for a tyrosine kinase, and can act as a substrate for an arginine methyltransferase.

4. An assay kit comprising the polypeptide according to claim 1, for the detection and quantification of tyrosine kinase activity or arginine methytransferase activity in cells.

* * * * *

UNITED STATES PATENT AND TRADEMARK OFFICE
CERTIFICATE OF CORRECTION

PATENT NO. : 6,300,473 B1 Page 1 of 1
DATED : October 9, 2001
INVENTOR(S) : Richard It is certified that error appears in the above-identified patent and that said Letters Patent is hereby corrected as shown below:

<u>Column 25,</u>
<400> SEQUENCE: 8: "Arg Ala Pro Pro Pro Ala" should read -- Arg Ala Pro Pro Pro
                                1                    5                                1                    5
Pro Ala --

Signed and Sealed this

Thirteenth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,300,473 B1
DATED         : October 9, 2001
INVENTOR(S)   : Richard It is certified that error appears in the above-identified patent and that said Letters Patent is hereby corrected as shown below:

Column 25,
Lines 50-51, "substrate for arginine methyltransferase." should read -- substrate for an arginine methyltransferase. --

Column 26,
Line 53, "methytransferase" should read -- methyltransferase --

Signed and Sealed this

Seventeenth Day of June, 2003

JAMES E. ROGAN
*Director of the United States Patent and Trademark Office*